(12) United States Patent
Yoshida et al.

(10) Patent No.: US 6,426,434 B1
(45) Date of Patent: Jul. 30, 2002

(54) PROCESS FOR THE SYNTHESIS OF UREA (75) Inventors: Kinichi Yoshida; Kenji Yoshimoto; Yasuhiko Kojima, all of Chiba (JP)

(73) Assignees: Toyo Engineering Corporation, Tokyo (JP); PT Pupuk Sriwidjaja, Palembang (ID)

( * ) Notice: Subject to any disclaimer, the term of this patent is extended or adjusted under 35 U.S.C. 154(b) by 0 days.

(21) Appl. No.: 09/984,486

(22) Filed: Oct. 30, 2001

(30) Foreign Application Priority Data

Nov. 1, 2000 (JP) ........................................ 2000-334395

(51) Int. Cl.$^7$ ............................................. C07C 273/04
(52) U.S. Cl. ............................ 564/71; 564/67; 564/69; 564/70; 564/72
(58) Field of Search ............................ 564/67, 69, 70, 564/71, 72

(56) References Cited

FOREIGN PATENT DOCUMENTS

| EP | 0 329 214 | 8/1989 |
|----|-----------|--------|
| JP | 60-166656 | 8/1985 |
| JP | 62-39559  | 2/1987 |
| JP | 62-39560  | 2/1987 |
| JP | 62-15070  | 4/1987 |
| JP | 63-112552 | 5/1988 |
| JP | 63-126857 | 5/1988 |
| JP | 10-182587 | 7/1998 |

*Primary Examiner*—Peter O'Sullivan
(74) *Attorney, Agent, or Firm*—Oblon, Spivak, McClelland, Maier & Neustadt, P.C.

(57) ABSTRACT

A urea synthesis process with improved heat economy, wherein a urea synthesis solution obtained by removing most of the unreacted ammonium carbamate by stripping with carbon dioxide at a pressure approximately equal to a urea synthesis pressure is subjected to a high and low pressure decomposition. The gas mixture obtained from the high-pressure decomposition is condensed in at least two steps. Gases obtained from the stripping of the urea synthesis solution, after an initial condensation may be alternatively routed into the high-pressure decomposition column thus facilitating the decomposition of unreacted ammonium carbamate; may be mixed with off-gases from the high-pressure decomposition column and routed to an indirect heat-exchanger for concentrating the aqueous urea solution and facilitating the condensation of the off-gases from the high pressure decomposition column; or may be routed to a condenser for the gas mixture obtained from the high-pressure decomposition after it has underwent indirect heat-exchange with the aqueous urea solution, thus facilitate the further condensation of these gases.

8 Claims, 3 Drawing Sheets

PROCESS FOR THE SYNTHESIS OF UREA

BACKGROUND OF THE INVENTION

1. Field of the Invention

The present invention is directed to an improved, more efficient and economical process for the synthesis of urea from carbon dioxide and ammonia:

$$2\,NH_3 + CO_2 \rightleftharpoons NH_2CONH_2 + H_2O.$$

This process involves reacting ammonia and carbon dioxide to form urea, followed by separation of unreacted ammonia and carbon dioxide by stripping with carbon dioxide at a pressure approximately equal to the urea synthesis pressure and by high and low pressure decomposition of residual ammonium carbamate. The process of the present invention efficiently uses off-gases from the high and low pressure decomposition and condensates of these gases and provides a more economical processes for synthesizing urea. For instance, improved conservation and recovery of heat provided by the present invention reduces process costs and improves the overall efficiency and economy of urea synthesis.

2. Description of the Related Art

Urea is synthesized by reacting carbon dioxide and ammonia at a high temperature and pressure. Conventionally, this reaction is performed inside of a urea synthesis zone or reactor at a suitable pressure and temperature for synthesis of urea and involves the formation and subsequent dehydration of ammonium carbamate to form urea:

As shown above, the formation of ammonium carbamate and its subsequent dehydration into urea essentially occur simultaneously yielding urea. However, purity and yield of urea in the resulting reaction mixture (urea synthesis solution) can be improved by stripping using carbon dioxide and by high-pressure decomposition of ammonium carbonate.

Processes for obtaining urea from carbon dioxide and ammonia are known, see Japanese Patent Laid-Open No. 10-182587. Urea may be synthesized by the following process steps:

reacting ammonia and carbon dioxide at a urea synthesis pressure and a urea synthesis temperature to form a urea synthesis solution, separating the unreacted ammonium carbamate from the urea synthesis solution as a gas mixture of ammonia, carbon dioxide and water by bringing the solution into contact with carbon dioxide at a pressure substantially equal to the urea synthesis pressure, condensing the resulting gas mixture and recycling the condensate to the urea synthesis zone, further treating the urea synthesis solution from which the unreacted ammonium carbamate is separated to obtain an aqueous urea solution, and concentrating the aqueous urea solution.

In the above-described method, after stripping and condensation of the off-gases from the stripper, an uncondensed gas mixture containing inert gas, ammonia, carbon dioxide and water remains. This uncondensed gas mixture is washed in a scrubber using an absorption medium to absorb ammonia and carbon dioxide in the uncondensed gas mixture. After scrubbing substantially only the inert gas is discharged from the scrubber to the outside of the system.

Japanese Patent Laid-Open No. 61-109760, discloses that such an inert gas may be introduced into the high pressure decomposition step of the unreacted ammonium carbamate remaining in the urea synthesis solution after carbon dioxide stripping.

Other urea synthesis methods attempt to concentrate the aqueous urea solution formed by the above reactions using the condensation heat generated from condensation of the off-gases from the high pressure decomposition step, see e.g. Japanese Patent Publication No. 62-15070, Japanese Patent Laid-Open No. 63-112552, Japanese Patent Laid-Open No. 62-39559, Japanese Patent Laid-Open No. 60-166656, Japanese Patent Laid-Open No. 62-39560, Japanese Patent Laid-Open No. 63-126857, and EP A1 0329214).

Figure 1:
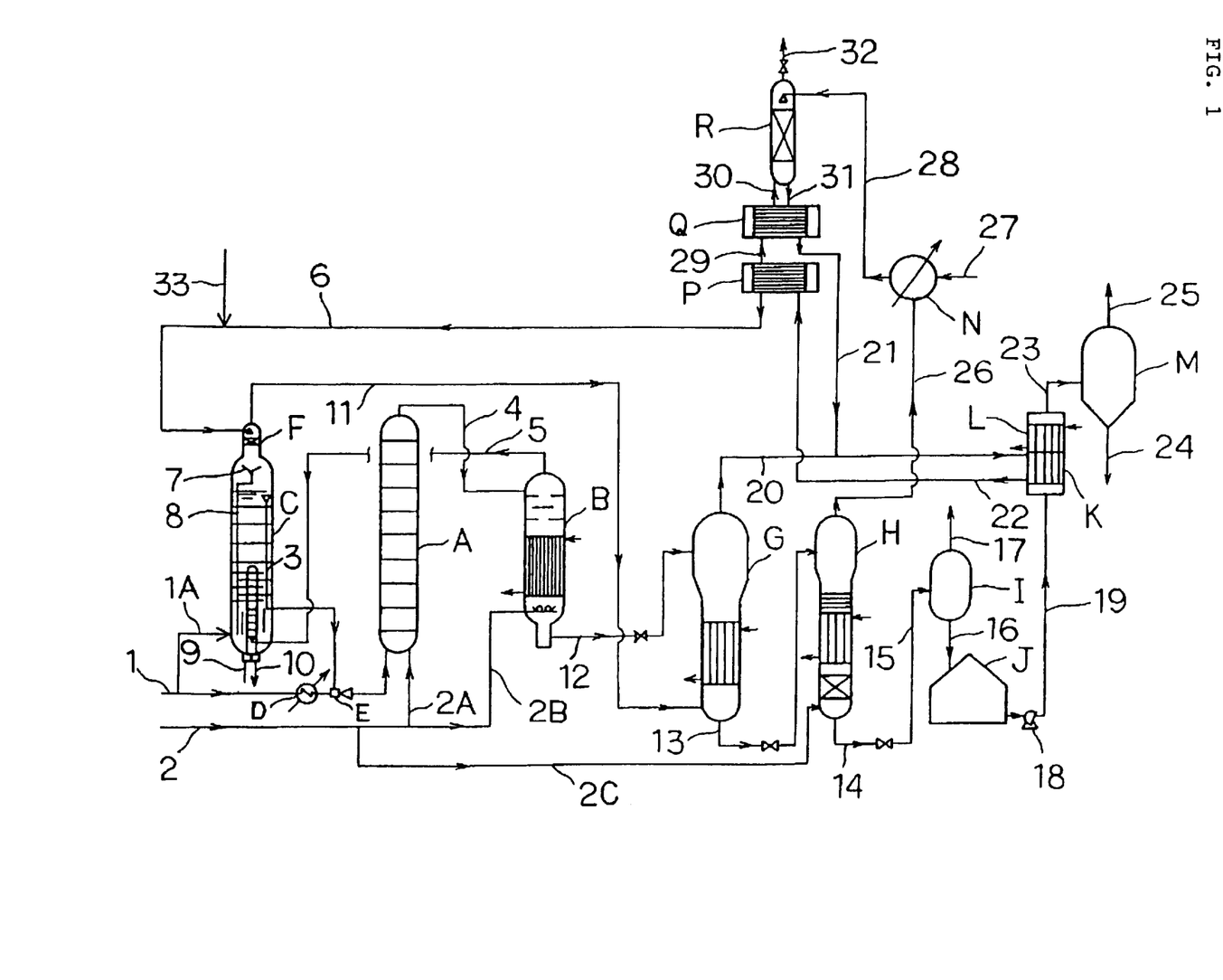
FIG. 1 is a flow sheet showing an embodiment of the present invention where an uncondensed gas mixture from the stripper and scrubber is introduced into the high-pressure decomposition.
Figure 2:
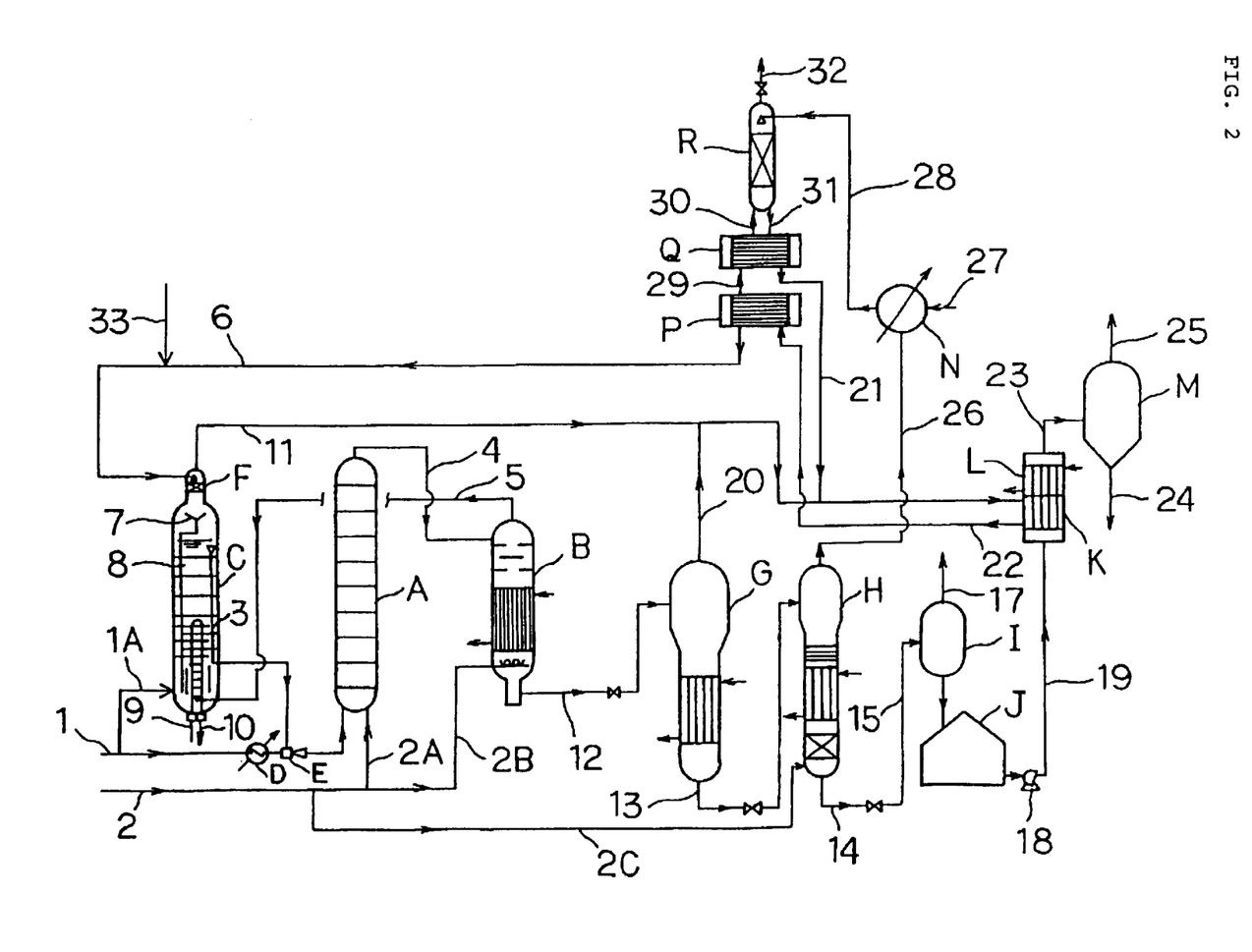
FIG. 2 is a flow sheet showing an embodiment of the present invention where an uncondensed gas mixture from the stripper and scrubber is introduced into the condensation by indirect heat-exchange.
Figure 3:
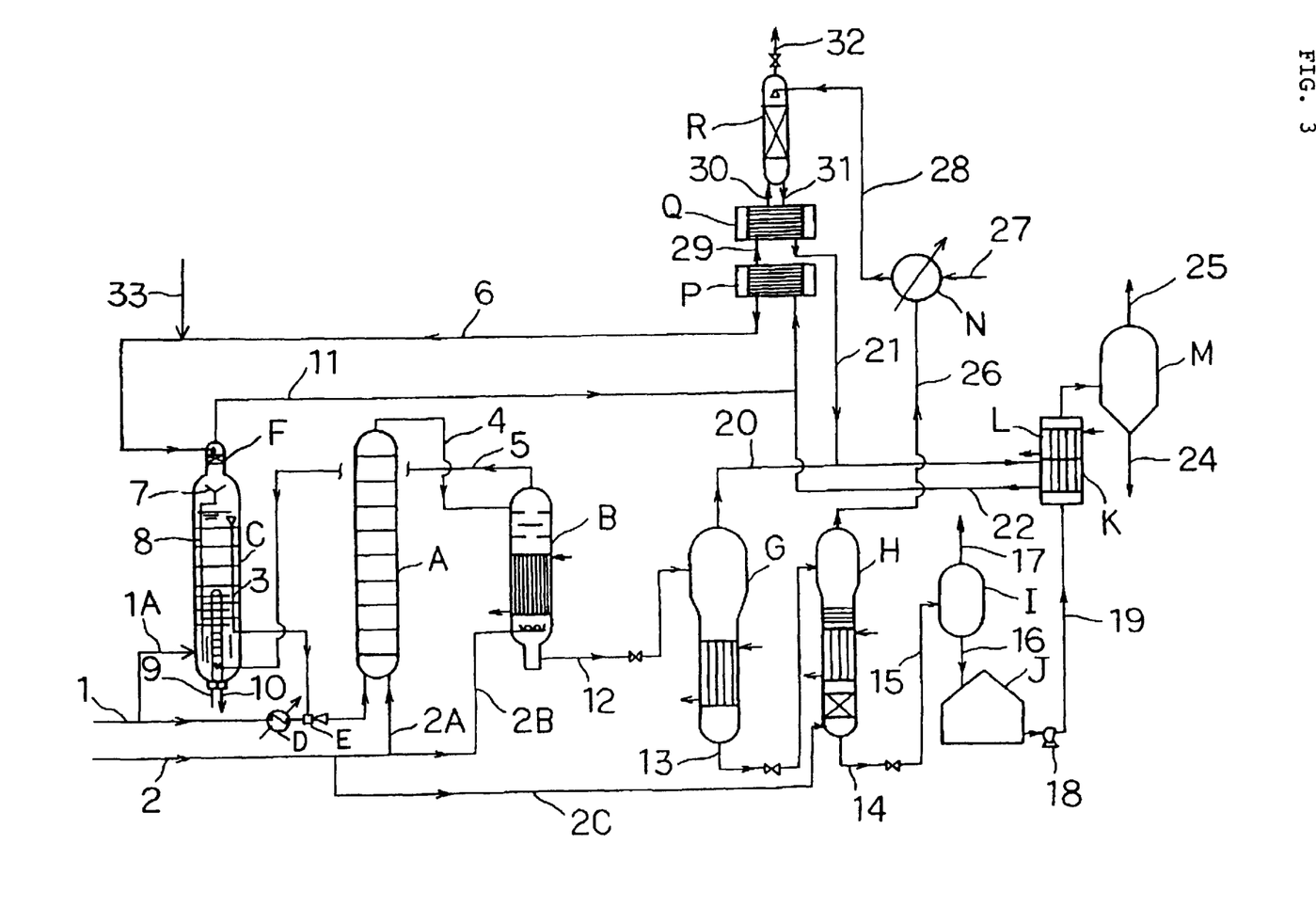
FIG. 3 is a flow sheet showing an embodiment of the present invention where an uncondensed gas mixture from the stripper and scrubber is introduced into the condensing of the high-pressure gas mixture from the high-pressure decomposition step.

However, the above-described methods do not describe the improved heat recovery, efficiencies and economies provided by the present invention, in which the off-gases from the high pressure decomposition of the unreacted ammonium carbamate in the urea synthesis solution are condensed in at least two steps, the condensate is recycled to the scrubber, and the uncondensed gases from the scrubber are routed as shown in FIGS. 1, 2 and 3.

SUMMARY OF THE INVENTION

One object of the present invention is to provide a process with improved heat economy for synthesizing urea that comprises stripping unreacted ammonium carbamate using carbon dioxide (e.g. raw material carbon dioxide) under a pressure equal to the urea synthesis pressure. In the present invention, the phrases, "condense a gas mixture" or "condensing a gas mixture", may optionally encompass condensing and washing a gas mixture, condensing and absorbing a gas mixture, or both.

The above-described object of the present invention may be achieved by the following urea synthesis process:

(1) Reacting carbon dioxide, which may contain a slight amount of oxygen for corrosion prevention, with ammonia at pressure and temperature suitable for the synthesis of urea in a urea synthesis zone or reactor, thus forming a urea synthesis solution;

bringing the urea synthesis solution into contact with carbon dioxide at a pressure substantially equal to the urea synthesis pressure to separate a major or substantial part of the unreacted ammonium carbamate contained in the urea synthesis solution as a gas mixture of ammonia, carbon dioxide and water;

condensing the resulting gas mixture and recycling the condensate into the urea synthesis zone or reactor;

subjecting the urea synthesis solution having a major or substantial part of the unreacted ammonium carbamate removed to a high pressure decomposition, preferably at about 1 to 4 Mpa, thereby separating unreacted ammonium carbamate remaining in the urea synthesis solution as a gas mixture of ammonia, carbon dioxide and water;

subjecting the resulting urea synthesis solution containing the remaining unreacted ammonium carbamate to low pressure decomposition, preferably at about 1 to 0.5 MPa, in at least one stage, thereby separating the substantially all of the remaining unreacted ammonium carbamate as a gas mixture of ammonia, carbon dioxide and water to obtain an aqueous urea solution;

cooling and condensing the low pressure gas mixture separated in the low pressure decomposition to obtain a low pressure condensate;

condensing the off-gases from the high-pressure decomposition of ammonium carbamate by:

contacting them with a condensate of the off-gases from the high and low pressure decompositions of ammonium carbamate, and by indirectly exchanging heat with the aqueous urea solution to condense the high pressure gas mixture to obtain condensate of the gases from the high-pressure decomposition;

utilizing the condensation heat generated at that time for at least a part of the heat source for concentrating the aqueous urea solution; and introducing the high pressure condensate (see e.g. line 6 in FIGS. 1, 2 and 3) into the condensation step for the gas mixture obtained from stripping the urea synthesis solution with carbon dioxide at a pressure substantially equal to the urea synthesis pressure (see e.g. element "B" in FIGS. 1, 2, and 3);

wherein the high pressure gas mixture resulting from the high pressure decomposition of unreacted ammonium carbamate is condensed by indirect heat exchange with the aqueous urea solution (e.g. condensing element K in FIGS. 1, 2 and 3), followed by at least two condensations and a washing (e.g. as respectively shown in P, Q and R in FIGS. 1, 2 and 3).

The condensation of the high-pressure gas mixture or off-gases resulting from the high-pressure decomposition may be carried out by:

condensing the high-pressure gas mixture from the high-pressure decomposition step (e.g. line 20 in FIGS. 1, 2 and 3) by mixture with condensates of gases obtained from the high and low pressure decomposition of ammonium carbamate and by indirect heat-exchange with aqueous urea solution (see e.g. "K" in FIGS. 1, 2 and 3);

condensing remaining high-pressure gas mixture in a first condensation zone or first condenser (e.g. "P" in FIGS. 1, 2 and 3) and recycling the liquid condensate to a scrubber (e.g. scrubber "F" in FIGS. 1, 2 and 3).

condensing remaining high-pressure gas mixture from the prior condensation step in a second condensation zone or second condenser (e.g. "Q" in FIGS. 1, 2 and 3), bringing any remaining uncondensed ammonia and carbon dioxide into contact with the pressurized, low-pressure condensate from low-pressure decomposition of unreacted ammonium carbamate (e.g. from col. H in FIGS. 1, 2 and 3) in the step of washing (e.g. "R" in FIGS. 1, 2 and 3) and optionally discharging inert gas from the washing step.

Other objects of the present invention include:

(2) The process as described above in section (1), wherein the uncondensed gas mixture containing inert gas, ammonia, carbon oxide, and water obtained from stripping the urea synthesis solution (e.g. from stripper "B" in FIGS. 1, 2 and 3) and from the scrubber (e.g. scrubber "B" in FIGS. 1, 2 and 3) is introduced into the high pressure decomposition (e.g. "G" in FIG. 1) to decompose the unreacted ammonium carbamate.

(3) The process as described in above in section (1), wherein the uncondensed gas mixture containing inert gas, ammonia, carbon oxide, and water obtained from stripping the urea synthesis solution (e.g. from stripper "B" in FIGS. 1, 2 and 3) and from the scrubber (e.g. scrubber "B" in FIGS. 1, 2 and 3) is introduced into the step of condensing by indirect heat exchange (e.g. "L" in FIG. 2) to condense at least a part of ammonia, carbon dioxide and water in the gas mixture.

(4) The process as described in above in section (1), wherein the uncondensed gas mixture containing inert gas, ammonia, carbon oxide, and water obtained from stripping the urea synthesis solution (e.g. from stripper "B" in FIGS. 1, 2 and 3) and from the scrubber (e.g. scrubber "B" in FIGS. 1, 2 and 3) is introduced into the step of first cooling and condensing (e.g. "P" in FIG. 3) to condense at least a part of ammonia, carbon dioxide and water in the gas mixture.

In the present invention, gas from a high pressure decomposition column is condensed in at least two steps (or in three steps including the condensation occurring in the aqueous urea solution heating apparatus). Moreover, gas from a scrubber may also be condensed together with the gas from the high-pressure decomposition. Thus, the temperature in the condensing part of the aqueous urea solution heating apparatus can be increased and heat recovery can efficiently be carried out. Owing to the presence of oxygen from the scrubber, apparatus corrosion can also be avoided.

Further, the present invention allows the use of condensates having a pressure equal to the pressure of the high pressure decomposition column as an absorption medium for gases from the high pressure decomposition column without requiring a further increase of pressure.

DESCRIPTION OF THE PREFERRED EMBODIMENTS

In the present invention, the urea synthesis conditions are preferably as follows:

a pressure ranging from about 13 to 25 MPaG, a temperature ranging from about 180 to 200° C., the mole ratio (N/C) of ammonia to carbon dioxide ranging from about 3.0 to 4.0, and the mole ratio (H/C) of water to carbon dioxide of approximately 1 or lower.

The conditions for stripping the urea synthesis solution from the urea synthesis with raw material carbon dioxide are preferably as follows: the pressure is approximately equal to the urea synthesis pressure and the temperature ranges from about 160 to 200° C.

The gas mixture of ammonia, carbon dioxide and water separated by stripping the urea synthesis solution is introduced into the bottom part of a condensation zone (condenser). The condensation conditions are preferably about 160 to 180° C. for the temperature, about 3.0 to 4.5 for N/C and approximately 1 or lower for H/C. The gas mixture is condensed by contacting it with an aqueous ammonium carbamate solution residing in a condenser and at that time, whereby condensation heat is generated. The condensation heat is recovered by generation of low pressure steam.

The gas mixture of an inert gas, ammonia, carbon dioxide and water which is not condensed in the condensation zone is introduced into a scrubber installed in the top part of the condensation zone and washed with the condensate of a gas mixture from high pressure decomposition, which will be described later. The resulting washing solution is introduced into the bottom of the condensation zone through a down pipe installed in the condensation zone. Most of ammonia and carbon dioxide in the above-described gas mixture are absorbed and together with remaining ammonia and carbon dioxide to discharge the inert gas from the scrubber. The discharged inert gas is utilized for stripping, as it will be described later, preferably in the high pressure decomposition.

In the condensation step, the condensate flows down through the down pipe laid in the condensation zone and having an opening in the upper part, enter an ejector derived by raw material ammonia having a pressure of about 15 to 30 MPa and a temperature of about 100 to 200° C., whereby the pressure of the condensate is increased by about 0.2 to 1 Mpa. The condensate is then introduced into the urea synthesis zone (e.g. element "A" in FIGS. 1, 2 and 3).

The pressure of the urea synthesis solution from the stripping step is reduced to about 1 to 4 MPaG, preferably 1.5 to 2.5 MPaG, and introduced into the high pressure decomposition step to decompose the unreacted ammonium carbamate remaining in the synthesis solution to a gas mixture of ammonia, carbon dioxide and water at the temperature of 120 to 170° C. At that time, the inert gas from the above-described scrubber may be introduced into the high pressure decomposition to be used as a stripping agent. In such a manner, the unreacted ammonium carbamate remaining in the aqueous urea solution can be decreased.

The aqueous urea solution from the high pressure decomposition still contains a small amount of the unreacted ammonium carbamate. The aqueous urea solution is further decreased in pressure to about 0.1 to 0.5 MPaG and the unreacted ammonium carbamate is decomposed at about 100 to 130° C. At that time, some of raw material carbon dioxide may be used as a stripping agent. In such a manner, ammonia in the aqueous urea solution can be substantially removed.

The aqueous urea solution containing substantially no ammonia from the low pressure decomposition (e.g. element "H" in FIGS. 1, 2 and 3) is introduced into a concentration (evaporation) apparatus through a pipe side of an indirect heat exchanger. On the other hand, the gas mixture from the high pressure decomposition is introduced into the trunk part of the indirect heat exchanger to be heat-exchanged with the aqueous urea solution. The aqueous urea solution is heated by condensation heat generated at that time. In such a manner, the condensation heat of the high pressure gas mixture is utilized for concentrating the aqueous urea solution. Incidentally, the aqueous urea solution heated by the condensation heat may further be heated by low pressure steam. The concentration is preferably carried out at about 100 to 130° C. On the other hand, the condensation of the high pressure gas mixture is preferably carried-out at about 100 to 120° C. The condensation may be carried out under a normal or reduced pressure.

The condensate and the uncondensed gas mixture from the indirect heat exchanger are introduced into a first zone of high pressure condensation where the uncondensed gas mixture is partially condensed under cooling. The remaining uncondensed gas mixture is further introduced into a second zone of the high pressure condensation while the resulting condensate is fed to a scrubber to be used for absorbing the ammonia and carbon dioxide in the uncondensed gas mixture. In the second step of the high pressure condensation, the gas mixture is further condensed under cooling and the condensate is introduced into the trunk part of the indirect heat exchanger (e.g. element "K" in FIGS. 1, 2 and 3) to be used for the condensation of the high pressure gas obtained from the high pressure decomposition step (e.g. element "G" in FIGS. 1, 2 and 3).

The uncondensed gas still remaining in the second step of the high pressure condensation mainly contains inert gas, but is further washed with an absorption medium in a washing column (e.g. element R in FIGS. 1, 2 and 3) to remove residual ammonia and carbon dioxide from the inert gas. The remaining inert gas is discharged out of the top of the washing column. The washing solution from the bottom part of the washing column is fed to the second step of the high pressure condensation (e.g. element "Q" in FIGS. 1, 2 and 3).

The gas mixture containing the inert gas from the scrubber (e.g. scrubber "F" in FIGS. 1, 2 and 3) may be used as a stripping agent in the high pressure decomposition (see e.g. FIG. 1, element "G"); alternatively it may be mixed together with the gas mixture from the high pressure decomposition and introduced into the trunk part of the indirect heat exchanger for heating the aqueous urea solution (see e.g. FIG. 2, element "K"); alternatively, it may also be directly introduced to a first step of high pressure condensation of the gas mixture from the high pressure decomposition to be condensed (see e.g. FIG. 3, element "P").

Hereinafter, the present invention is concretely described with the reference to the attached drawings.

With the reference to FIG. 1 which is a flow sheet showing an embodiment of the present invention, a part of liquid ammonia with the pressure of about 15 to 30 MPaG from the line 1 is preheated to about 100 to 200° C. with high or low pressure steam in a preheater D and then fed to the driving side of an ejector E to increase the pressure of a condensate aspirated through a down pipe 3 of a condenser C by 0.2 to 1 Mpa. The ammonia from the ejector E is introduced into the bottom part of a urea synthesis column A together with carbon dioxide containing about 0.2 to 5% by volume of air as oxygen.

Lines 2, 2A, 2B and 2C are lines for introducing carbon dioxide, which may contain a slight amount of oxygen, into the apparatus.

The urea synthesis column A is operated at a pressure ranging from about 13 to 25 MPaG, a temperature ranging from about 180 to 200° C., an N/C ratio of about 3.5 to 5.0, and an H/C ratio of about 1.0 or less. The introduced ammonia, carbon dioxide, and the condensate are converted to urea while rising in the synthesis column and the produced urea synthesis solution is introduced into the top part of a stripper B at a pressure substantially equal to the urea synthesis pressure through the line 4.

While flowing down in the stripper B, the urea synthesis solution is brought into contact with carbon dioxide fed in counter flow through a line 2B at 160 to 200° C. to separate the unreacted ammonium carbamate contained in the urea synthesis solution as a gas mixture of ammonia, carbon dioxide, an inert gas and water.

The separated gas mixture is introduced into the bottom part of the condenser C through the line 5. The gas mixture is brought into contact with a washing liquid flowing down from a scrubber F installed in the top part through a washing liquid receiver 7 and a down pipe 8 to the bottom part of the condenser to be condensed at 170 to 190° C. The condensation heat generated at that time is eliminated by generating steam from water introduced from a line 9 and discharged through a line 10. The resulting condensate flows down in the down pipe 3 having the opening in the upper part of the condenser and is introduced, as described above, into the synthesis column A through the ejector E. The remaining of the liquid ammonia from the line 1 is supplied to the condenser C through a line 1A to maintain the N/C ratio at 3.0 to 4.5 and the H/C ratio at 1 or less in the condensate in the condenser C.

A high pressure absorption solution, which will be described later, is introduced into the scrubber F to wash the uncondensed gas mixture of the inert gas, ammonia, and carbon dioxide, thereby absorbing a part of ammonia and carbon dioxide in the gas mixture. A gas mixture of mainly an inert gas is discharged from the top part of the scrubber.

The pressure of the urea synthesis solution from which the major part of the unreacted ammonium carbamate is separated in the stripper B is reduced to a preferable pressure of from 1.2 to 2.5 MPaG and the solution is then introduced through a line 12 into a high pressure decomposition column G and heated to 120 to 160° C. to decompose most of the unreacted ammonium carbamate. At that time, the inert gas from the line 11 is introduced into the bottom part of the high pressure decomposition column G as a stripping agent to make separation of the unreacted ammonium carbamate easy. A gas mixture of ammonia, carbon dioxide, the inert gas and water is discharged through a line 20 from the top of the column.

The resulting urea synthesis solution from which most of the unreacted ammonium carbamate is separated in the high pressure decomposition column G flows through the line 13 and after the pressure of the solution is reduced to 0.1 to 0.5 MPaG, the solution is introduced into the top of a low pressure decomposition tower H and heated to 110 to 140° C. to separate the substantially all of the remaining unreacted ammonium carbamate as a gas mixture of ammonia, carbon dioxide and water. At that time, any of the raw material carbon dioxide may be introduced as a stripping agent from a line 2C into the bottom part of the low pressure decomposition column. The separated gas mixture is discharged through a line 26. An aqueous urea solution discharged from the bottom part of the low pressure decomposition column H through a line 14 is introduced through the line 15 into a gas-liquid separator I after the pressure is decreased to a normal pressure, and the gas mixture of ammonia, carbon dioxide and water in a slight amount is separated and discharged through a line 17. The resulting aqueous urea solution is introduced into an aqueous urea solution storage tank J through a line 16.

The aqueous urea solution from the aqueous urea solution storage tank J flows through a line 19 and is fed to a condensing part K and then a heating part L of an aqueous urea solution heating apparatus by means of a pump 18 to be heated. The urea solution is then introduced into a concentration apparatus M through a line 23 to be concentrated, and the concentrated urea solution is taken out through a line 24. At the time of concentration, the evaporated steam accompanied with slight amounts of ammonia and carbon dioxide is discharged through a line 25. The gas mixture from the line 20 and a condensate from a line 21, which will be described later, are introduced into the trunk side of the condensing part K of the aqueous urea solution heating apparatus to be condensed by indirect heat exchange with the aqueous urea solution flowing in the pipe side. The aqueous urea solution is heated with the condensation heat of the gas mixture generated at that time. The temperature of the trunk part of the condensing part K is kept at 100 to 120° C. Steam is introduced into the trunk part of the heating part L of the aqueous urea solution heating apparatus to heat the aqueous urea solution flowing in the pipe side to about 110 to 138° C. The condensed liquid and the uncondensed gas mixture obtained in the condensation part of the aqueous urea solution heating apparatus are introduced into the trunk part of a first condenser P through a line 22 and are cooled by water flowing in the pipe side to be condensed. The temperature of the trunk side of the first condenser P is kept at about 90 to 120° C. The produced condensate is sent to the scrubber F through a line 6.

Water may be introduced into line 6 by way of line 33.

In the first condenser P, the uncondensed gas mixture is introduced into the trunk part of a second condenser Q through a line 29 and condensed under cooling by being brought into contact with a high pressure washing solution, which will be described later, introduced through the line 31. The obtained condensate is sent to the condensing part K of the aqueous urea solution heating apparatus as described above through the line 21. The temperature of the trunk side of the second condenser Q is kept at about 40 to 70° C. The gas mixture which is not condensed in the trunk side of the second condenser Q is introduced through a line 30 into a washing column and brought into contact with the low pressure condensate introduced from the top part through a line 28 and pressurized at a pressure of about 1.2 to 2.5 MPaG to absorb substantially all of the remaining ammonia and carbon dioxide. The inert gas that is not absorbed is discharged out through the line 32.

The gas mixture separated in a lower pressure decomposition column H is sent to a low pressure condenser N, and brought into contact under cooling with an aqueous diluted ammonium carbonate solution (which may contain a slight amount of urea) introduced through the line 27, which solution has absorbed slight amounts of ammonia and carbon dioxide from lines 17, 25 (and a gas mixture separated in a condenser if there is the condenser after the low pressure decomposition column H) to be condensed to be a low pressure condensate which is then introduced from the line 28 into the washing column R after the pressure is increased.

Another embodiment will be described with the reference to FIG. 2. In this embodiment, the different point from the embodiment described along with FIG. 1 is only that the gas mixture of an inert gas, ammonia, carbon dioxide and water from the scrubber F is directly fed to the condensing part K through a line 11.

Further, another embodiment will be described with the reference to FIG. 3. In this embodiment, the different point from the embodiment described along with FIG. 1 is only that the gas mixture of an inert gas, ammonia, carbon dioxide and water from the scrubber F is directly fed to the second condenser through a line 11.

Exemplary embodiments of the present invention are now described with reference to FIGS. 1, 2 and 3 which respectively describe the embodiments of Examples 1, 2 and 3. Table 1, which appears after Example 3 below, provides a side-by-side stoichiometric comparison of the processes of Examples 1, 2 and 3. The processes of the present invention may be described by particular discrete steps described in a particular order, however, it is understood that these processes involve the interaction of multiple components and interrelation of different steps. Therefore, while the various process steps are interrelated as described, the invention may be alternatively described by different orderings of steps which describe the same overall process. While these particular embodiments exemplify aspects of the present invention, it is understood that the present invention is not restricted only to these embodiments.

EXAMPLE 1

The process shown in FIG. 1 was carried out as follows. The urea synthesis reaction was conducted at the temperature of 182° C. and the pressure of 15.2 MPaG in an urea synthesis column by introducing 39,588.75 kg/hr of liquid ammonia heated to 140° C. by a preheater D through line 1, 7,140.00 kg/hr of raw material carbon dioxide through line 2A which was supplied in 52,639.17 kg/hr together with 1,205 kg/hr of air and an inert gas through line 2, and a condensate containing 50,604.46 kg/hr of urea, 57,049.10 kg/hr of ammonia, 45,132.18 kg/hr of carbon dioxide, 36,655.50 kg/hr of water, and 154.59 kg/hr of biuret through down pipe 3.

The resulting urea synthesis solution containing:

77,240.55 kg/hr of urea, 81,517.63 kg/hr of ammonia, 32,729.53 kg/hr of carbon dioxide, 44,657.29 kg/hr of water, and 179.58 kg/hr of biuret was introduced into a stripper B through a line 4 and brought into contact with 43,342.92 kg/hr of the raw material carbon dioxide introduced from the bottom part through a line 2B and the major part of unreacted ammonium carbamate was separated as a gas mixture containing:

66,607.50 kg/hr of ammonia, 61,227.50 kg/hr of carbon dioxide, and 6,442.92 kg/hr of water.

The separated gas mixture was introduced into the bottom part of condenser C and while rising through condenser C, was brought into contact with a high pressure condensate containing:

249.17 kg/hr of urea, 19,154.99 kg/hr of ammonia, 22,909.59 kg/hr of carbon dioxide, and 15,205.00 kg/hr of water and introduced through a line 6 to the top part of a scrubber F disposed at the top of the condenser C.

From the top of a scrubber F, a gas mixture containing:

1,137.92 kg/hr of ammonia, 1,969.17 kg/hr of carbon dioxide, 1,205.00 kg/hr of an inert gas, and 155.42 kg/hr of water was discharged out through a line 11.

The urea synthesis solution discharged from the bottom of the stripper B containing:

73,500.87 kg/hr of urea, 16,970.74 kg/hr of ammonia, 17,481.46 kg/hr of carbon dioxide, 37,134.84 kg/hr of water, and 301.67 kg/hr of biuret was sent through line 12 and decreased in the pressure to 1.72 MPaG, and then introduced into the top of a high pressure decomposition column G, and brought into contact with the gas mixture introduced into the bottom part of the column G through line 11 in a counter-flow at 155° C. and most of the unreacted ammonium carbamate was separated as a gas mixture containing:

10,497.36 kg/hr of ammonia, 16,841.16 kg/hr of carbon dioxide, 1,205.00 kg/hr of an inert gas, and 3,516.68 kg/hr of water through line 20.

The urea synthesis solution containing:

72,747.30 kg/hr of urea, 8,010.27 kg/hr of ammonia, 3,112.75 kg/hr of carbon dioxide, 33,567.62 kg/hr of water, and 358.95 kg/hr of biuret was discharged from the bottom part of the column G through line 13, decreased in the pressure to 0.25 MPaG, introduced into the top part of a low pressure decomposition column H, and heated to 123° C.

A gas mixture containing:

7,644.32 kg/hr of ammonia, 5,148.89 kg/hr of carbon dioxide, and 3,198.30 kg/hr of water was discharged from the top part of column H.

On the other hand, from the bottom part of the column of column H, an aqueous urea solution containing:

72,230.09 kg/hr of urea, 663.15 kg/hr of ammonia, 492.02 kg/hr of carbon dioxide, 30,217.42 kg/hr of water, and 367.25 kg/hr of biuret was taken out through line 14. After the pressure was decreased, the aqueous urea solution was sent through line 15 to a gas-liquid separator I where residual ammonia and carbon dioxide were removed. The resulting aqueous urea solution and was sent to storage tank J through line 16. From this storage tank the aqueous urea solution is available for concentration and further processing in elements K, L and M shown in FIG. 1.

The-gas mixture obtained from low pressure decomposition column H was introduced into a low pressure condenser N through line 26 and brought into contact under cooling with an aqueous diluted ammonium carbonate solution containing a slight amount of urea (from line 27) and was condensed. This condensate of gases from the low pressure decomposition contained:

249.17 kg/hr of urea, 8,664.30 kg/hr of ammonia, 6,075.10 kg/hr of carbon dioxide, and 11,169.99 kg/hr of water.

This condensate was introduced into the top part of washing column R through line 28 and brought into contact with a gas rising from the bottom part of column R to absorb ammonia and carbon dioxide from the rising gas thereby obtaining a washing solution containing:

249.17 kg/hr of urea, 9,052.21 kg/hr of ammonia, 6,078.85 kg/hr of carbon dioxide, and 11,184.15 kg/hr of water.

The washing solution was introduced into a second condenser Q through line 31. The inert gas that was not absorbed was discharged out through a line 32. The washing solution was brought into contact at 51° C. with a gas mixture containing:

5,990.82 kg/hr of ammonia, 1,684.14 kg/hr of carbon dioxide, 1,023.48 kg/hr of water, and 1,205.00 of an inert gas from line 29 to obtain a condensate containing:

249.17 kg/hr of urea, 14,648.45 kg/hr of ammonia, 7,752.55 kg/hr of carbon dioxide, and 12,171.80 kg/hr of water.

The gas mixture (394.58 kg/hr of ammonia, 10.42 kg/hr of carbon dioxide, 35.83 kg/hr of water, and 1,205.00 kg/hr of the inert gas) that was not condensed was introduced into the bottom part of the washing column R through a line 30 and was washed.

The condensate was introduced into the trunk side of the condensing part K of the aqueous urea solution heating apparatus through line 21 and condensed at a temperature of 110° C. together with the gas mixture from the high pressure decomposition column G introduced through line 20 while being indirectly heat-exchanged with the aqueous urea solution sent through line 19 from the aqueous urea solution storage tank J. Line 22 exits the indirect heat-exchanger and contained an uncondensed gas mixture of:

10,507.73 kg/hr of ammonia, 7,408.84 kg/hr of carbon dioxide, 1,544.14 kg/hr of water, and 1,205.00 kg/hr of the inert gas, and a condensate of:

249.17 kg/hr of urea, 14,638.08 kg/hr of ammonia, 17,184.87 kg/hr of carbon dioxide, and 14,144.35 kg/hr of water the contents of line 22 were introduced into a first condenser P and condensed under cooling at 100° C. to obtain a condensate containing:

249.17 kg/hr of urea, 19,154.99 kg/hr of ammonia, 22,909.59 kg/hr of carbon dioxide, and 14,665.00 kg/hr of water.

The resulting condensate from condenser P was mixed with 540 kg/hr of water added from line 33 for sealing a pump, and this mixture was introduced into the top part of the scrubber F through line 6. The uncondensed gas mixture (a gas mixture containing 5,990.82 kg/hr of ammonia, 1,684.14 kg/hr of carbon dioxide, 1,023.48 kg/hr of water, and 1,205.00 kg/hr of the inert gas) in the first condenser P was sent to a second condenser Q through line 29 and condensed to obtain the condensate mentioned above that is introduced into line 21.

The aqueous urea solution stored in tank J as described above, was introduced into condensing part K of the aqueous urea solution heating apparatus, then into heating part L of the aqueous urea solution heating apparatus and then further heated by steam and introduced into a concentration apparatus M through a line 23 to obtain urea solution containing approximately 95% urea by weight.

EXAMPLE 2

This example was carried out along the process shown in FIG. 2. In the process, since the gas mixture from a line 11 was to be introduced directly to the condensing part K of the aqueous urea solution heating apparatus, the liquids and the gas compositions after the high pressure decomposition were as follows. Incidentally, the operation conditions were controlled to be substantially the same as those used in Example 1. The reaction contents at various points in the process shown in FIG. 2 are described below:

At the High pressure decomposition column G:

gas composition in line 20:
ammonia 8,623.33 kg/hr

| | |
|---|---|
| ammonia | 8,623.33 kg/hr |
| carbon dioxide | 13,611.25 kg/hr |
| water | 3,510.00 kg/hr | urea synthesis solution composition in line 13:

| | |
|---|---|
| urea | 72,747.30 kg/hr |
| ammonia | 8,746.37 kg/hr |
| carbon dioxide | 4,373,49 kg/hr |
| water | 33,418.89 kg/hr |
| biuret | 358.95 kg/hr |

At the Low pressure decomposition column H:

gas composition in line 26:

| | |
|---|---|
| ammonia | 8,380.43 kg/hr |
| carbon dioxide | 6,409.63 kg/hr |
| water | 3,049.56 kg/hr | aqueous urea solution in line 14:

| | |
|---|---|
| urea | 72,230.09 kg/hr |
| ammonia | 655.14 kg/hr |
| carbon dioxide | 492.02 kg/hr |
| water | 30,217.13 kg/hr |
| biuret | 367.25 kg/hr |

At the washing column R:

liquid composition in line 28:

| | |
|---|---|
| urea | 249.17 kg/hr |
| ammonia | 9,400.41 kg/hr |
| carbon dioxide | 7,335.84 kg/hr |
| water | 11,021.25 kg/hr | liquid composition in line 31:

| | |
|---|---|
| urea | 249.17 kg/hr |
| ammonia | 9,788.32 kg/hr |
| carbon dioxide | 7,339.59 kg/hr |
| water | 11,035.41 kg/hr | gas composition in line 30:

| | |
|---|---|
| ammonia | 394.58 kg/hr |
| carbon dioxide | 10.42 kg/hr |
| water | 35.83 kg/hr |
| the inert gas | 1,205.00 kg/hr | gas composition in line 32:

| | |
|---|---|
| ammonia | 6.67 kg/hr |
| carbon dioxide | 6.67 kg/hr |
| water | 21.67 kg/hr |
| inert gas | 1,205.00 kg/hr |

At the second condenser Q:

liquid composition in line 21:

| | |
|---|---|
| urea | 249.17 kg/hr |
| ammonia | 14,964.47 kg/hr |
| carbon dioxide | 8,887.21 kg/hr |
| water | 12,066.34 kg/hr |

At condensation part K of the aqueous urea solution heating apparatus:

gas composition in the line 11:

| | |
|---|---|
| ammonia | 1,137.92 kg/hr |
| carbon dioxide | 1,969.17 kg/hr |
| water | 155.42 kg/hr |
| the inert gas | 1,205.00 kg/hr | liquid composition in line 22:

| | |
|---|---|
| urea | 249.17 kg/hr |
| ammonia | 14,954.82 kg/hr |
| carbon dioxide | 17,613.42 kg/hr |
| water | 14,122.33 kg/hr | gas composition in line 22:

| | |
|---|---|
| ammonia | 9,770.89 kg/hr |
| carbon dioxide | 6,854.21 kg/hr |
| water | 1,609.43 kg/hr |
| the inert gas | 1,205.00 kg/hr |

At the first condenser P:

liquid composition in line 6:

| | |
|---|---|
| urea | 249.17 kg/hr |
| ammonia | 19,154.99 kg/hr |
| carbon dioxide | 22,909.59 kg/hr |
| water | 14,665.00 kg/hr | gas composition in line 29:

| | |
|---|---|
| ammonia | 5,570.73 kg/hr |
| carbon dioxide | 1,558.04 kg/hr |
| water | 1,066.76 kg/hr |
| the inert gas | 1,205.00 kg/hr |

At the concentration apparatus M:

aqueous urea solution in line 19:

| | |
|---|---|
| urea | 72,230.09 kg/hr |
| ammonia | 467.34 kg/hr |
| carbon dioxide | 342.72 kg/hr |
| water | 27,111.52 kg/hr |
| biuret | 367.52 kg/hr | aqueous urea solution in line 24:

| | |
|---|---|
| urea | 71,922.45 kg/hr |
| ammonia | 0 kg/hr |
| carbon dioxide | 0 kg/hr |
| water | 3810.89 kg/hr |
| biuret | 484.48 kg/hr |

EXAMPLE 3

This example was carried out as shown in FIG. 3, but the operation conditions were controlled to be substantially the same as those used in Example 1. In this embodiment, the gas mixture from line 11 was introduced directly to the trunk part of the first condenser P. The liquid and the gas compositions after the high pressure decomposition were as follows.

At the high pressure decomposition column G:

gas composition in line 20:

| | |
|---|---|
| ammonia | 8,623.33 kg/hr |
| carbon dioxide | 13,611.25 kg/hr |
| water | 3,510.00 kg/hr | urea synthesis solution composition in line 13:

| | |
|---|---|
| urea | 72,747.30 kg/hr |
| ammonia | 8,746.37 kg/hr |
| carbon dioxide | 4,373.49 kg/hr |
| water | 33,418.89 kg/hr |
| biuret | 358.95 kg/hr |

At the low pressure decomposition column H:

gas composition in line 26:

| | |
|---|---|
| ammonia | 8,380.43 kg/hr |
| carbon dioxide | 6,409.63 kg/hr |
| water | 3,049.56 kg/hr | aqueous urea solution in line 14:

| | |
|---|---|
| urea | 72,230.09 kg/hr |
| ammonia | 655.14 kg/hr |
| carbon dioxide | 492.02 kg/hr |
| water | 30,217.13 kg/hr |
| biuret | 367.25 kg/hr |

At the washing column R:

liquid composition in the line 28:

| | |
|---|---|
| urea | 249.17 kg/hr |
| ammonia | 9,400.41 kg/hr |
| carbon dioxide | 7,335,84 kg/hr |
| water | 11,021.25 kg/hr | liquid composition in line 31:

| | |
|---|---|
| urea | 249.17 kg/hr |
| ammonia | 9,788.32 kg/hr |
| carbon dioxide | 7,339.59 kg/hr |
| water | 11,035.41 kg/hr | gas composition in line 30:

| | |
|---|---|
| ammonia | 394.58 kg/hr |
| carbon dioxide | 10.42 kg/hr |
| water | 35.83 kg/hr |
| the inert gas | 1,205.00 kg/hr | gas composition in line 32:

| | |
|---|---|
| ammonia | 6.67 kg/hr |
| carbon dioxide | 6.67 kg/hr |
| water | 21.67 kg/hr |
| the inert gas | 1,205.00 kg/hr |

At the second condenser Q:

In line 21:

| | |
|---|---|
| urea | 249.17 kg/hr |
| ammonia | 14,963.83 kg/hr |
| carbon dioxide | 9,137.91 kg/hr |
| water | 12,124.13 kg/hr |

At condensation part K of the aqueous urea solution heating apparatus:

liquid composition in line 22:

| | |
|---|---|
| urea | 249.17 kg/hr |
| ammonia | 14,955.31 kg/hr |
| carbon dioxide | 16,761.24 kg/hr |
| water | 14,092.94 kg/hr | gas composition in line 22:

| | |
|---|---|
| ammonia | 8,631.85 kg/hr |
| carbon dioxide | 5,987.92 kg/hr |
| water | 1,541.19 kg/hr |

At the first condenser P:

liquid composition in line 6:

| | |
|---|---|
| urea | 249.17 kg/hr |
| ammonia | 19,154.99 kg/hr |
| carbon dioxide | 22,909.59 kg/hr |
| water | 14,665.00 kg/hr | gas composition in line 11:

| | |
|---|---|
| ammonia | 1,137.92 kg/hr |
| carbon dioxide | 1,969.17 kg/hr |
| water | 155.42 kg/hr |
| the inert gas | 1,205.00 kg/hr | gas composition in line 29:

| | |
|---|---|
| ammonia | 5,570.09 kg/hr |
| carbon dioxide | 1,808.74 kg/hr |
| water | 1,124.55 kg/hr |
| the inert gas | 1,205.00 kg/hr |

At the concentration apparatus M:

aqueous urea solution in line 19:

| | |
|---|---|
| urea | 72,230.09 kg/hr |
| ammonia | 467.34 kg/hr |
| carbon dioxide | 342.72 kg/hr |
| water | 27,111.52 kg/hr |
| biuret | 367.52 kg/hr | aqueous urea solution in line 24:

| | |
|---|---|
| urea | 71,922.45 kg/hr |
| ammonia | 0 kg/hr |
| carbon dioxide | 0 kg/hr |
| water | 3810.89 kg/hr |
| biuret | 484.48 kg/hr |

Table I which follows, compares the embodiments of Examples 1, 2 and 3.

| | Ex. 1 | Ex. 2 | Ex. 3 |
|---|---|---|---|
| Column G--high pressure decomposition | | | |
| line 20 (gas) | | | |
| ammonia | 10,497.36 | 8,623.33 | 8,623.33 |
| carbon dioxide | 16,841.16 | 13,611.25 | 13,611.25 |

-continued

| | Ex. 1 | Ex. 2 | Ex. 3 |
|---|---|---|---|
| water | 3,516.68 | 3,510.00 | 3,510.00 |
| inert gas | 1,205.00 | 0 | 0 |
| line 13 (urea synthesis solution) | | | |
| urea | 72,747.30 | 72,747.30 | 72,747.30 |
| ammonia | 8,010.27 | 8,746.37 | 8,746.37 |
| carbon dioxide | 3,112.75 | 4,373.49 | 4,373.49 |
| water | 33,567.62 | 33,418.89 | 33,418.89 |
| biuret | 358.95 | 358.95 | 358.95 |
| line 11 (gas) | | | |
| ammonia | 1,137.92 | N/A | N/A |
| carbon dioxide | 1,969.17 | N/A | N/A |
| water | 155.42 | N/A | N/A |
| inert gas | 1,205.00 | N/A | N/A |
| Column H--low pressure decomposition | | | |
| line 26 (gas) | | | |
| ammonia | 7,644.32 | 8,380.43 | 8,380.43 |
| carbon dioxide | 5,148.89 | 6,409.63 | 6,409.63 |
| water | 3,198.30 | 3,049.56 | 3,049.56 |
| line 14 (aqueous solution) | | | |
| urea | 72,230.09 | 72,230.09 | 72,230.09 |
| ammonia | 663.15 | 655.14 | 655.14 |
| carbon dioxide | 492.02 | 492.02 | 492.02 |
| water | 30,217.42 | 30,217.13 | 30,217.13 |
| biuret | 367.25 | 367.25 | 367.25 |
| Column R--washing | | | |
| line 28 (liquid) | | | |
| urea | 249.17 | 249.17 | 249.17 |
| ammonia | 8,664.30 | 9,400.41 | 9,400.41 |
| carbon dioxide | 6,075.10 | 7,335.84 | 7,335.84 |
| water | 11,169.99 | 11,021.25 | 11,021.25 |
| line 31 (liquid) | | | |
| urea | 249.17 | 249.17 | 249.17 |
| ammonia | 9,052.21 | 9,788.32 | 9,788.32 |
| carbon dioxide | 6,078.85 | 7,339.59 | 7,339.59 |
| water | 11,184.15 | 11,035.41 | 11,035.41 |
| line 30 (gas) | | | |
| ammonia | 394.58 | 394.58 | 394.58 |
| carbon dioxide | 10.42 | 10.42 | 10.42 |
| water | 35.83 | 35.83 | 35.83 |
| inert gas | 1,205.00 | 1,205.00 | 1,205.00 |
| line 32 (gas) | | | |
| ammonia | 6.67 | 6.67 | 6.67 |
| carbon dioxide | 6.67 | 6.67 | 6.67 |
| water | 21.57 | 21.67 | 21.67 |
| inert gas | 1,205.00 | 1,205.00 | 1,205.00 |
| Condenser Q (second condenser) | | | |
| line 21 (liquid) | | | |
| urea | 249.17 | 249.17 | 249.17 |
| ammonia | 14,648.45 | 14,964.47 | 14963.83 |
| carbon dioxide | 7,752.55 | 8,887.21 | 9137.91 |
| water | 12,171.80 | 12,066.34 | 12124.13 |
| Condensation part K | | | |
| line 11 (gas) | | | |
| ammonia | N/A | 1,137.92 | N/A |
| carbon dioxide | N/A | 1,969.17 | N/A |
| water | N/A | 155.42 | N/A |
| inert gas | N/A | 1,025.00 | N/A |
| line 22 (liquid) | | | |
| urea | 249.17 | 249.17 | 249.17 |
| ammonia | 14,638.08 | 14,954.82 | 14,955.31 |
| carbon dioxide | 17,184.87 | 17,613.42 | 16,761.24 |
| water | 14,144.35 | 14,122.33 | 14,092.94 |

-continued

| | Ex. 1 | Ex. 2 | Ex. 3 |
|---|---|---|---|
| line 22 (gas) | | | |
| ammonia | 10,507.73 | 9,770.89 | 8,631.85 |
| carbon dioxide | 7,408.84 | 6,854.21 | 5,987.92 |
| water | 1,544.14 | 1,609.43 | 1,541.19 |
| inert gas | 1,205.00 | 1,205.00 | 0 |
| Condenser P (first condenser) | | | |
| line 6 (liquid) | | | |
| urea | 249.17 | 249.17 | 249.17 |
| ammonia | 19,154.99 | 19,154.99 | 19,154.99 |
| carbon dioxide | 22,909.59 | 22,909.59 | 22,909.59 |
| water | 14,665.00 | 14,665.00 | 14,665.00 |
| line 11 (gas) | | | |
| ammonia | N/A | N/A | 1,137.92 |
| carbon dioxide | N/A | N/A | 1,969.17 |
| water | N/A | N/A | 155.42 |
| inert gas | N/A | N/A | 1,205.00 |
| line 29 (gas) | | | |
| ammonia | 5,990.82 | 5,570.73 | 5,570.09 |
| carbon dioxide | 1,684.14 | 1,558.04 | 1,808.74 |
| water | 1,023.48 | 1,066.76 | 1,124.55 |
| inert gas | 1,205.00 | 1,205.00 | 1,205.00 |
| Concentration Apparatus M | | | |
| line 19--aqueous urea solution | | | |
| urea | 72,230.09 | 72,230.09 | 72,230.09 |
| ammonia | 467.34 | 467.34 | 467.34 |
| carbon dioxide | 342.72 | 342.72 | 342.72 |
| water | 27,111.52 | 27,111.52 | 27,111.52 |
| biuret | 367.52 | 367.52 | 367.52 |
| line 24--aqueous solution | | | |
| urea | 71,922.45 | 71,922.45 | 71,922.45 |
| ammonia | — | — | — |
| carbon dioxide | — | — | — |
| water | 3,810.89 | 3,810.89 | 3,810.89 |
| biuret | 484.48 | 484.48 | 484.48 |

Modifications and Other Embodiments

Various modifications and variations of the described processes for synthesizing urea as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the chemical, chemical engineering arts or related fields are intended to be within the scope of the following claims.

INCORPORATION BY REFERENCE

Each document, patent application or patent publication cited by or referred to in this disclosure is incorporated by reference in its entirety. The priority document of the present application, Japanese Patent Application 2000-334395, filed Nov. 1, 2000, is herein incorporated by reference.

What is claimed is:

1. A process for synthesizing urea comprising:
   (a) reacting carbon dioxide with ammonia at temperature and pressure suitable for synthesis of urea in a urea synthesis zone to form a urea synthesis solution;
   (b) stripping said urea synthesis solution with carbon dioxide at a pressure substantially equal to the urea synthesis pressure to decompose unreacted ammonium carbamate contained in the urea synthesis solution as a gas mixture of ammonia, carbon dioxide and water;

(c) condensing the gas mixture obtained from (b) and recycling the condensate into the urea synthesis zone;

(d) decomposing at high pressure the unreacted ammonium carbamate in the urea synthesis solution obtained from stripping the urea synthesis solution, thereby decomposing unreacted ammonium carbamate remaining in the stripped urea synthesis solution into a gas mixture of ammonia, carbon dioxide and water;

(e) decomposing at low pressure unreacted ammonium carbamate in the urea synthesis solution obtained from the high pressure decomposition, thereby obtaining a low pressure gas mixture of ammonia, carbon dioxide and water, and obtaining an aqueous urea solution substantially free of unreacted ammonium carbamate;

(f) condensing the low pressure gas mixture obtained from the low pressure decomposition to obtain a condensate of the low pressure gas mixture;

(g) condensing the high pressure gas mixture obtained from the high pressure decomposition of the urea synthesis solution by:

(i) contacting it with a condensate of gases obtained from the high and low pressure decomposition of the urea synthesis solution, (ii) indirectly contacting the mixture of (i) with aqueous urea solution under conditions suitable for indirect heat exchange, thus heating the aqueous urea solution and obtaining a partially condensed mixture of gases, (iii) introducing the partially condensed mixture of gases (ii) into a first cooling and condensation zone under conditions suitable for further condensation of said mixture of gases, and recycling the resulting condensate to (c) to facilitate cooling and condensation of the gases obtained from (b), (iv) introducing the remaining uncondensed mixture of gases (iii) into a second cooling and condensation zone under conditions suitable for further condensation of said mixture of gases, and mixing the resulting condensate with the off-gases from high-pressure decomposition (d), (v) washing the remaining uncondensed gases from (iv) with a washing solution comprising the pressurized condensate of gases from low pressure decomposition (f), introducing said washing solution to the second cooling zone (iv), and optionally discharging inert gas.

2. The process of claim 1, wherein the carbon dioxide contains a slight amount of oxygen for corrosion protection.

3. The process of claim 1, wherein the high pressure decomposition is performed at a pressure ranging from 1 to 4 Mpa.

4. The process of claim 1, wherein the low pressure decomposition is performed at a pressure ranging from 0.1 to 0.5 Mpa.

5. The process of claim 1, wherein the aqueous urea solution in (g) is further heated by steam.

6. The process of claim 1, wherein the uncondensed gas mixture obtained from condensing the gases obtained by stripping (b) the urea synthesis solution is introduced into the high pressure decomposition (d) of ammonium carbamate.

7. The process of claim 1, wherein the uncondensed gas mixture obtained from condensing the gases obtained by stripping (b) the urea synthesis solution is mixed with the gas mixture from the high-pressure decomposition (d) and the mixture is used to indirectly heat the aqueous urea solution.

8. The process of claim 1, wherein the uncondensed gas mixture obtained from condensing the gases obtained by stripping (b) the urea synthesis solution is introduced into a condenser for condensing uncondensed gases obtained from the high-pressure decomposition after the gas mixture from the high-pressure decomposition is partially condensed by indirect heat exchange with the aqueous urea solution.

* * * * *